(12) United States Patent
Matsuda et al.

(10) Patent No.: US 7,615,344 B2
(45) Date of Patent: Nov. 10, 2009

(54) PROCESS FOR PRODUCING EXTRACT FOR CELL-FREE PROTEIN SYNTHESIS AND CELL EXTRACT PRODUCED THEREBY

(75) Inventors: Natsuko Matsuda, Yokohama (JP); Takanori Kigawa, Yokohama (JP); Namtip Chumpolkulwong, Yokohama (JP); Chie Takemoto, Yokohama (JP); Mikako Shirouzu, Yokohama (JP); Akiko Tanaka, Yokohama (JP); Shigeyuki Yokoyama, Yokohama (JP)

(73) Assignee: Riken, Wako-shi (JP)

( * ) Notice: Subject to any disclaimer, the term of this patent is extended or adjusted under 35 U.S.C. 154(b) by 217 days.

(21) Appl. No.: 11/282,613

(22) Filed: Nov. 21, 2005

(65) Prior Publication Data
US 2006/0134735 A1 Jun. 22, 2006

Related U.S. Application Data

(63) Continuation of application No. PCT/JP2004/006948, filed on May 21, 2004.

(30) Foreign Application Priority Data

| May 22, 2003 | (JP) | ............................ 2003-145221 |
| Mar. 31, 2004 | (JP) | ............................ 2004-105251 |

(51) Int. Cl.
*C12Q 1/68* (2006.01)
(52) U.S. Cl. ..................................... 435/6
(58) Field of Classification Search ............. None
See application file for complete search history.

(56) References Cited

FOREIGN PATENT DOCUMENTS

| EP | 1857558 | * | 11/2007 |
| JP | 4-200390 | A | 7/1992 |
| JP | 7-110236 | A | 11/1995 |
| WO | WO-88/08453 | A1 | 11/1988 |
| WO | WO-01/83805 | A2 | 11/2001 |

OTHER PUBLICATIONS

Shehata et al. Journal of Bacteriology, vol. 124, No. 2, pp. 857-862, Nov. 1975.*
Patterson et al. Biochemical Genetics, vol. 8, No. 2, pp. 205-230, 1973.*
Klammt et al., Methods in Molecular Biology., In vitro transcription protocols, second edition, edited by G. Grandis, humana Press Inc., Totowa NJ, vol. 375, pp. 57-78, 2007.*
Matthews and Korner, Eur. J. Biochem., vol. 17, pp. 328-338, 1970.*
Zawada et al. Abstracts of Papers American Chemical Society, vol. 224, No. 1- 2, p. BIOT 91, XP009068071, (2002).
Jones, P.G. et al., J. Biol. Chem., 1992, vol. 174, No. 12, pp. 3903-3914.
Geoffrey Zubay, Annual Review of Genetics, 1973, vol. 7, pp. 267-287.
Wang et al., "An Optimized Yeast Cell-Free System:Sufficient For Translation of Human Papillomavirus 58 L1 mRNA and Assembly of Virus-Like Particles." Journal of Bioscience Bioengineering, vol. 106, No. 1, pp. 8-15: (2008).
Hofbauer et al., "Preparation of a mRNA-Dependent Cell-Free Translation System From Whole Cells of *Saccharomyces cerevisiae*," Eur. J. Biochem, vol. 122, pp. 199-203, (1982).
Kim, R.G. et al., "Expression-Independent Consumption of Substrates in Cell-Free Expression System From *Escherichia coli*," Journal of Biotechnology, vol. 84, pp. 27-32, (2000).
Kim, Ho-Cheol et al., "Continuous Cell-Free Protein Synthesis Using Glycolytic Intermediates as Energy Sources," J. Microbiol. Biotechnol., vol. 18, No. 5, pp. 885-888, (2008).
Zubay, Geoffrey, "In Vitro Synthesis of Protein in Microbial System," Department of Biological Sciences, Columbia University, New York City, pp. 267-288, (1973).
Ertola et al., "Design, Formulation, and Optimization of Media," Bioprocess Technol., vol. 21, pp. 89-137, (1995).
Lee et al., "Statistical Medium Formulation and Process Modeling by Mixture Design of Experiment for Peptide Overexpression in Recombinant *Escherichia coli*," Applied Biochem. And Biotech., vol. 135, pp. 81-100, (2006).
Takanori Kigawa, Biophysics, 2000, vol. 40, No. 6, pp. 391-394.
Jones, P.G. et al., J. Biol. Chem., 1992, vol. 174, No. 12, pp. 3903-3914.
Geoffrey Zubay, Annual Review of Genetics, 1973, vol. 7, pp. 267-287.

* cited by examiner

*Primary Examiner*—Gary Benzion
*Assistant Examiner*—Cynthia B Wilder
(74) *Attorney, Agent, or Firm*—Birch, Stewart, Kolasch & Birch, LLP.

(57) ABSTRACT

It is intended to provide a process for producing an extract for cell-free protein synthesis whereby the productivity of a protein and the production efficiency can be improved. Cells are cultured under suppressed growth conditions. In the stationary phase of the culture, the cells are collected and then disrupted. The above-described cells are preferably bacterial cells, in particular, *Escherichia coli* cells. In the suppressed growth conditions as described above, the culture temperature is preferably from 20 to 32° C., more preferably 26° C. or higher and lower than 30° C.

5 Claims, 6 Drawing Sheets

(a) Growth Curves of *E. coli* Cultured at 37°

(b) Growth Curves of *E. coli* Cultured at 30°C (c) Growth Curves of *E. coli* Cultured at 26°C (a) Growth Curves of *E. coli* Cultured at 37°C (b) Growth Curves of *E. coli* Cultured at 30°C (c) Growth Curves of *E. coli* Cultured at 26°C (a) Log Phase at 37°C (b) Stationary Phase at 37°C (c) Log Phase at 26°C (d) Stationary Phase at 26°C

```
                        SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Synthetic PCR 5' primer M13-45 Fw

<400> SEQUENCE: 1
ccagggtttt cccagtcacg ac                                           22

<210> SEQ ID NO 2
<211> LENGTH: 26
<212> TYPE: DNA
<213> ORGANISM: Artificial sequence
<220> FEATURE:
<223> OTHER INFORMATION: Synthetic PCR 3' primer M13 Rev

<400> SEQUENCE: 2
aatttcacac aggaaacagc tatgac                                       26
```

PROCESS FOR PRODUCING EXTRACT FOR CELL-FREE PROTEIN SYNTHESIS AND CELL EXTRACT PRODUCED THEREBY

CROSS-REFERENCE TO RELATED APPLICATIONS

The present application is a continuation of International application PCT/JP2004/006948, filed on May 21, 2004, and claims priority to Japanese application No. 2003-145221 filed on May 22, 2003 and Japanese application No. 2004-105251 filed on Mar. 31, 2004, which are hereby incorporated by reference in their entirety.

TECHNICAL FIELD

The present invention relates to a process for producing an extract for cell-free protein synthesis, in particular, a process for producing an extract having an improved productivity while maintaining the high protein synthetic activity, by preparing from cells at stationary phase in a suppressed growth condition, as well as an extract and a kit for cell-free protein synthesis produced by the process. The present invention also relates to a process for producing a protein using a cell-free protein synthesis system comprising an E. coli extract produced by the above process and a linear template DNA encoding the protein.

BACKGROUND ART

A cell-free protein synthesis system using a cell extract has been mainly utilized for identification of gene products and for investigation of their functions. For example, the system enables to analyze synthesized protein functions in the enzymatic activity and DNA binding capability and the like, or determine the molecular weight of translated products by labeling them with radioisotopes. Recently, techniques for increasing the amount production drastically in the system have been developed (e.g. see Patent References 1 and 2), and the system has been utilized also for protein structure analysis by X-ray crystallography, NMR and the like.

As extracts for carrying out the translation reaction, those derived from E. coli, wheat germ, and rabbit reticulocyte are commercially available. In an E. coli extract, it is known that transcription-translation coupled reaction can be used for synthesizing a protein directly from DNA. Such a method as using an E. coli S30 extract has been systematically developed by Zubay et al (e.g. see Non-patent Reference 1). The S30 extract contains ribosomes that are necessary for translation of mRNA; aminoacyl-tRNA synthetase; and initiation factors (IF), elongation factors (EF) and release factors (RF) for polypeptide chain synthesis. When a DNA template is used for protein synthesis, a DNA construct, in which a target protein gene is inserted downstream of a strong promoter (typically T7 promoter), is added in the system together with a T7 RNA polymerase and ribonucleotides to couple both reactions of transcription and translation. Due to the requirement of ATP and GTP for synthesis of aminoacyl-tRNA and translation reaction with mRNA, these are added to the cell-free system as energy sources with regeneration systems such as a creatine kinase/creatine phosphate system. With the above components, protein synthetic reaction in a cell is reconstituted in vitro.

Such an E. coli S30 extract can be prepared by growing E. coli in an appropriate culture medium, homogenizing the obtained cells, and centrifuging the cell homogenate at 30,000×g to obtain the prescribed supernatant. Generally, the culture temperature of E. coli is 37° C., and the cells are harvested at the growth stage from middle to late logarithmic growth phase of an elevated protein synthetic activity (e.g. see Patent Reference 3). The reason for use of the cells in logarithmic growth phase is that the synthetic activity of S30 extract is notably decreased when the growth stage of E. coli enters into stationary phase from logarithmic growth phase.

However, as the cell number of E. coli in a unit culture medium in the logarithmic growth phase is fewer than that in the stationary phase, there is a problem that production yield of extracts prepared from cells in the logarithmic growth phase is low. In addition, the growth time of E. coli is about 20 minutes in optimum growth conditions and this rapid growth causes another problem that the protein synthetic activity of S30 extract decreases due to the overgrowth of the cells if the cell harvesting time is not proper but late.

Recently, a transcription-translation coupled reaction system using eukaryotic cells such as wheat germ, rabbit reticulocyte or the like has been developed, however, it is necessary for such a system to use eukaryotic cells only at the specific stage of differentiation such as an early stage of development. In the conventional cell extracts, it is also a problem to cause an inactivation of transcription or translation system by degradations of mRNA and ribosomes affected by a group of contaminated nucleases, translation-inhibitory protein factors, proteases or the like during producing extracts or protein synthetic reaction.

In addition, in the recent post-genomic research field, the comprehensive analysis of structures and functions of various kinds of proteins has started, thus, it has become an essential object to improve the productivity and the workability of protein synthesis.

[Patent Reference 1]
Japanese Patent Kokoku publication No. JP-B-H07-110236.
[Patent Reference 2]
Japanese Patent Kokai publication No. JP-A-H04-200390
[Patent Reference 3]
Gazzete of International Publication No. 2001/83805
[Non-Patent Reference 1]
Geoffrey Zubay, Annual Review of Genetics, 1973, Vol. 7, pp. 267-287

DISCLOSURE OF THE INVENTION

Problems to be Solved by the Invention

Accordingly, it is an object of the present invention to provide a process for producing an extract for cell-free protein synthesis that enables to improve the productivity and workability of protein synthesis. In particular, it is an object to synthesize a protein more efficiently by controlling growth conditions of the cells used for the preparation of the extract.

Means to Solve the Problems

To solve the problems described above, the present inventors have studied the protein synthetic activities of the extracts obtained from E. coli cultured under a variety of growth conditions, and found the fact that, when the E. coli is cultured at a temperature lower than that of the optimum growth conditions, generally at 37° C., the ribosome content in the extract prepared from cells in the stationary phase is not decreased compared to that in the logarithmic growth phase, and a large amount of cell extract having a stable protein synthetic activity can be obtained. On the basis of this finding, the present invention has been completed.

According to a first aspect of the present invention, there is provided a process for producing an extract for cell-free protein synthesis comprising, culturing a cell under a suppressed growth condition, harvesting the cell at stationary phase in said culture, and disrupting said harvested cell. The cell is preferably a bacterial cell, in particular, an *Escherichia coli* cell. Further, the suppressed growth condition is preferably a condition to culture the cell at a temperature from 20° C. to 32° C., more preferably at a temperature of not lower than 26° C. and lower than 30° C.

In one embodiment of the present invention, there is provided a process for producing an extract for cell-free protein synthesis comprising the steps of culturing a *Escherichia coli* under a suppressed growth condition, harvesting the cell at stationary phase in said culture, and preparing S30 extract from said harvested *Escherichia coli* cell. The suppressed growth condition is preferably a condition to culture the cell at a culture temperature from 20° C. to 32° C., more preferably at a culture temperature of not lower than 26° C. and lower than 30° C.

In another aspect of the present invention, there is provided an extract of *Escherichia coli* for use in a cell-free protein synthesis, wherein said extract is produced by the process comprising the steps of culturing a *Escherichia coli* under a suppressed growth condition, harvesting the cell at stationary phase in said culture, and preparing S30 extract from said harvested *Escherichia coli* cells. The extract contains ribosomes that have an improved stability and/or an increased protein synthetic activity per unit amount of ribosome.

In a still another aspect of the present invention, there is provided a process for producing a protein using a cell-free protein synthesis system comprising an extract produced by the method described above, and a linear template DNA encoding the protein. The cell-free protein synthesis system is preferably a dialysis system.

In another embodiment of the present invention, a kit for use in a cell-free protein synthesis, comprising the *E. coli* extract described above is provided. The kit is preferably used for a cell-free protein synthetic reaction using a linear template DNA.

BEST MODE FOR CARRYING OUT THE INVENTION

Figure 1:
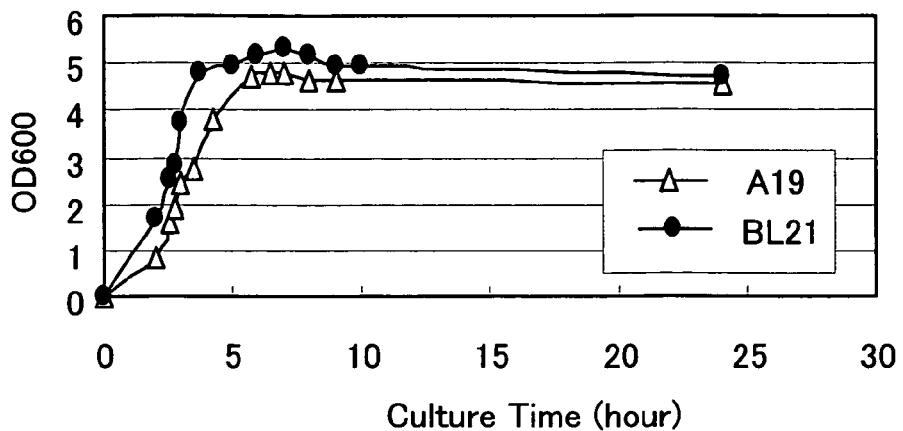
FIG. 1 shows the growth curves of *E. coli* BL21 and A19 strains cultured at (a) 37° C., (b) 30° C. or (c) 26° C. in example 1.
Figure 1:
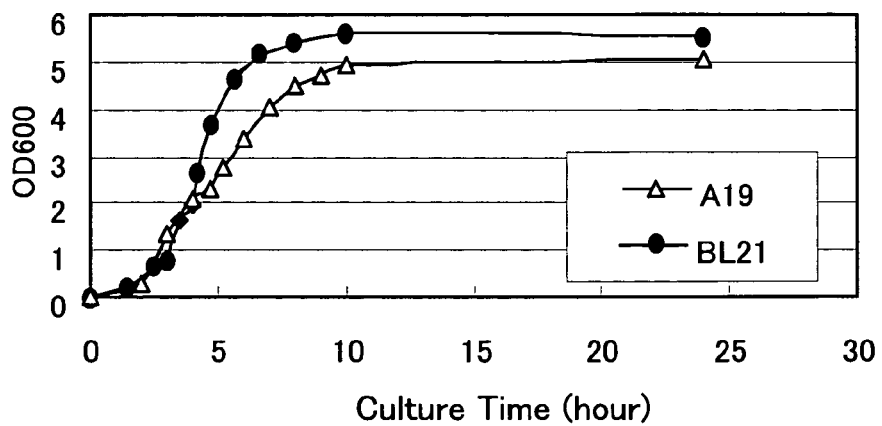
Figure 1:
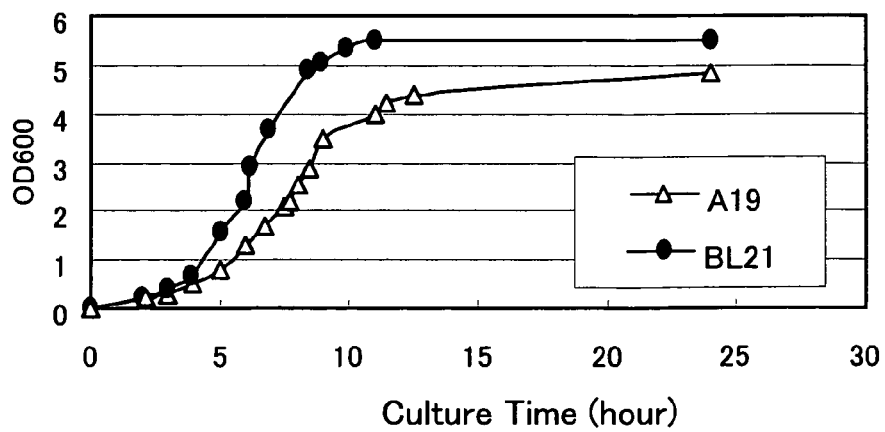

The cell-free protein synthesis system according to a method of the present invention is a system to synthesize a target protein by preparing an extract including protein factors necessary for translation of proteins, and reconstituting the reaction in vitro. The extracts derived from a variety of organisms can be used for constituting the cell-free system, for example, eukaryotic and prokaryotic cells extracts with high protein synthetic activities, obtained from bacteria including *E. coli*, thermophilic bacteria and the like, wheat germ, rabbit reticulocyte, mouse L cell, Ehrlich's ascitic cancer cell, HeLa cell, CHO cell and budding yeast and the like (see Clemens, M. J., Transcription and Translation—A Practical Approach, (1984), pp. 231-270; Henes, B. D. et al. eds., IRL Press, Oxford). Thus, a feature of the present invention is to culture these eukaryotic and prokaryotic cells under suppressed growth conditions.

In the present specification, the phrase "suppressed growth condition" means any non-optimum growth condition in viable environmental conditions for cells. Cells grow in a new environment, if it is suitable for the cells, while doing both metabolism (decomposition) and synthesis. Bacteria generally grow by division to double their cell numbers, Yeasts grow by budding, and fungi grow by elongation of mycelia. With respect to animal cells, only some kinds of cells such as bone marrow cells and hepatocytes can grow by division in vivo, but, even terminally differentiated cells can start to divide by malignant transformation and can be cultured in an in vitro culture dish. In this case, cells go through the preliminary lag phase and enter the logarithmic growth phase, during which the cell number increases exponentially. Then, according to the depletion of nutrients or oxygen, or reaching upper limit of cell density, the cells stop to grow and go into the stationary phase. The cell growth is regulated by a variety of environmental factors such as nutrients, temperature, pH, oxygen concentration, redox potential, water activity, pressure, and the like (Tetsuaki Tutido et al., Regulation of Microorganisms, Kodansha, 2002).

A suppressed growth condition according to a method of the present invention is any condition that at least one of the environmental factors is not optimum, but viable. For example, one of the important factors is temperature. Most chemical reactions in vivo are catalyzed by enzymes, therefore, a suitable temperature for growth of cells is generally around the ordinary temperature. In case of mesophilic bacteria such as *E. coli* and *Bacillus subtilis*, the optimum temperature is from 30° C. to 45° C. However, some of bacteria, in particular, called as thermophilic or psychrophilic bacteria inhabit at the higher or lower temperature, and grow in their respective optimum temperatures. Thus, an exemplary condition of the suppressed growth temperature is a temperature lower than the optimum temperature by 5 to 20° C. For example, as the optimum growth temperature of *E. coli* is about 37° C., it is preferably cultured at a temperature between 17° C. and 32° C. according to the present invention. At a temperature lower than 17° C., the growth of *E. coli* is extremely slow and cold stress responses may take place, while at a temperature higher than 32° C., the effect of the present invention can be hardly obtained. In addition, it is well known to a person skilled in the art that *E. coli* can grow at about 20° C. even though the growth rate is low. Thus, the temperature range of the present invention is preferably from 20 to 32° C., and more preferably not lower than 26° C. and lower than 30° C.

Facultative bacteria are viable in both anaerobic and aerobic conditions, but their growth in aerobic conditions is much faster than that in anaerobic conditions, such that the growth rate is generally ten times higher and more. Bacteria having the simplest auxotrophy, can grow with glucose and several mineral salts, but it is also known that addition of one or more of amino acids, various vitamins, or protein hydrolysate such as peptone to the medium composition, significantly accelerates the growth rate. Therefore, it is easy for a person having ordinary skill in the art to determine the optimum medium composition for each kind of cells, and to suppress the growth by removing one or several components from the medium.

Another important aspect of the present invention is to harvest the cells at stationary phase in the culture under the suppressed growth condition. In the present specification, the term, "stationary phase", refers to the stage in which growth rate of the cells is in equilibrium with the death rate due to decreasing the growth rate after logarithmic growth phase of the cell. When a cell is inoculated in a new container, firstly lag phase is observed for a while, during which the cell is adjusting to the new conditions. Next, the cell enters into logarithmic growth phase (also termed as "log phase" hereinafter) or exponential phase, and grows rapidly. Then, the cell is arrested to grow due to the limit of the container's capacity and deterioration of the culture broth, and enters to stationary phase. The term "logarithmic growth phase (log phase)" refers to a stage in which numbers of bacteria or cells are increasing exponentially. In general, cells in the log phase have higher protein synthetic activity, but lower cell density, compared to cells in the stationary phase, thus, to prepare a fixed volume of cells, it needs a larger volume of culture broth in the log phase than that in the stationary phase. Therefore, it will be very efficient if the S30 extract having a higher protein synthetic activity can be prepared using cells in the stationary phase by the method of the present invention.

As an *E. coli* extract, the S30 extract prepared by the method described in Zubay et al. (supra) or Pratt et al. (Pratt, J. M. et al. Transcription and Translation—A Practical Approach, (1984), pp. 179-209, Henes, B. D. et al. eds., IRL Press, Oxford) can be used. The *E. coli* S30 extract contains all the enzymes and factors from *E. coli* necessary for transcription and translation. Additionally, supplemental mixture can be added. A concrete method for preparation is as follows. First, *E. coli* is cultured and harvested by centrifugation and the like. The harvested cells are washed and resuspended in the buffer, and then lysed or broken with a French press, glass beads, Waring blender, or the like. The insoluble matter of disrupted *E. coli* cells is removed by centrifugation and the supernatant is then combined with a pre-incubation mixture and incubated. While this operation degrades the endogenous DNA and RNA, it may further include a step of adding a calcium salt or micrococcal nuclease to degrade intrinsic nucleic acids. The extract is then dialyzed to remove endogenous amino acids, nucleic acids, nucleosides and the like, and stored in liquid nitrogen or at −80° C. after dispensing appropriate aliquots.

As an eukaryotic cell extract, a rabbit reticulocyte lysate and a wheat germ extract are preferable. The rabbit reticulocyte lysate can be prepared by the method described in Pelham, H. R. B. and Jachson, R. J. Eur. J. Biochem., 67, 247-256, 1976. The wheat germ extract can be prepared, for example, by the method described in Roberts, B. E. and Paterson, B. M. Proc. Natl. Acad. Sci. USA, 70, 2330-2334, 1973.

When a protein synthetic reaction is carried out, the cell extract can be added with a template DNA or RNA for transcription/translation, substrate amino acids, energy sources, various ions, buffers, ATP regenerating systems, nuclease inhibitors, tRNAs, reducing agents, polyethylene glycol, cAMP, folic acids, antibacterial agents, substrates for RNA synthesis and RNA polymerase when using DNA as a template, and the like. These reaction mixtures can be prepared by selecting appropriate compositions in accordance with kinds of target proteins or employed protein synthesis systems. In case where *E. coli* S30 extract, it is supplemented with all or some of the followings: Tris-acetate, dithiothreitol (DTT), NTPs (ATP, CTP, GTP, and UTP), phosphoenol pyruvate, pyruvate kinase, at least one amino acid (20 naturally occurring amino acids including derivatives thereof. In case of labeling the protein with a radioisotope, the amino acids except the radio-labeled are added.), polyethylene glycol (PEG), folic acid, cAMP, tRNA, ammonium acetate, potassium acetate, potassium glutamate, magnesium acetate of optimized concentration, and the like. These supplemental solutions are usually stored separately from the S30 extract, and then combined just before use. Alternatively, the reaction mixture can be made by combining S30 extract and supplemental mixture, freezing and thawing the mixture to remove the RNA degradosomes (see International Publication WO 01/83805).

In a method of the present invention, an energy regenerating system can preferably be, but not limited to, an ATP regenerating system such as a combination of 0.02 to 5 µg/µl creatine kinase (CK) and 10 to 100 mM creatine phosphate (CP), or a combination of 1 to 20 mM phosphoenol pyruvate (PEP) and 0.01 to 1 µg/µl pyruvate kinase (PK). Each of the PK and CK is an enzyme that regenerates ATP from ADP, and requires PEP and CP as respective substrates.

These cell extracts and supplemental mixture can be distributed as a product easy for use in aliquots. These products can be stored at frozen or dried state, and put on the market as a kit in suitable containers for storage and for shipment. The kit can be accompanied by an instruction manual, a positive control DNA, a vector DNA and the like.

*E. coli* cell extracts produced by the inventive method comprises ribosomes having an improved stability. The term "improved stability" refers to that the stability of the extract is more improved in one or both of the process for preparing the extract and the cell-free protein synthesis process compared with the conventional extracts.

*E. coli* ribosome (referred to as 70S based on its sedimentation coefficient) consists of a pair of large and small subunits assembled to form a complex of millions of daltons. The small subunit (30S) controls the binding of mRNA and tRNA, and the large subunit (50S) catalyzes the formation of peptide bond. The 30S ribosomal subunit comprises one molecule of 16S ribosomal RNA (rRNA), and 21 kinds of different proteins (S1 to S21). The 50S subunit comprises a large 23S rRNA, a small 5S rRNA, and 34 different proteins (L1 to L34) that bind to the rRNAs. Therefore, it is supposed that the stability of ribosomes relates to the degradation or inactivation of each of the rRNAs and ribosomal proteins by a ribosome inactivation protein, ribonuclease, ribonucleotide phosphorylase, protease and the like. One of possible reasons for the improved stability of the *E. coli* extract produced by the inventive method may be due to the inhibition of degradation by these enzymes and the like in cells during culture or in the extract upon cell disruption.

Further, the *E. coli* cell extract produced by the inventive method comprises ribosomes that have an increased protein synthetic activity per unit ribosome amount. This increase of protein synthetic activity may be due to the improved stability of ribosome, or the suppression of production of other inhibitory factors, or the change of the three dimensional structure of ribosomes.

In the translation steps of proteins by ribosomes, various interactions of ribosomes with other factors at each step of the initiation, elongation, and termination of protein chain construction are important. In particular, it is important to form two functionally essential sites by association of two subunits, which constitute 70S ribosome. One is a binding site (P site) of tRNA bound to the elongating protein, and another is a binding site (A site) of tRNA that transfers additional amino acid to be bound. Therefore, ribosomes included in the inventive extract may form a three dimensional structure suitable for protein synthesis in the interaction with cofactors or mRNA.

In a still another embodiment of the present invention, there is provided a process for producing a protein using a cell-free protein synthesis system comprising an extract produced by the method described above, and a linear template DNA encoding the protein. In general, one of the factors affecting protein synthetic yield in cell-free synthesis system is the stability of template DNA. In particular, the influence is significant when a linear template DNA is used, such as PCR products and restriction enzyme digested fragments. It has been reported that the linear template DNA is highly susceptible to degradation by endogenous exonuclease in E. coli extracts (Pratt et al., Nucleic Acids Res., 9, 4459-4474, (1981); Benzinger et al., J. Virol., 15, 861-871, (1975); Lorenz and Wackernagel, Microbiol Rev., 58, 563-602, (1994)).

Such DNA exonucleases may accumulate, in particular, in E. coli cells cultivated for a long time. However, it has been revealed that the extract prepared with the method of the present invention from E. coli cells cultured at a low temperature, and harvested at a stationary phase, is highly suitable for protein synthesis by using a linear template DNA.

According to the embodiment, protein synthetic yield of cell-free system with a linear template DNA is significantly improved by preparing the extract from E. coli cells cultured under such a suppressed growth condition, and harvested at a stationary phase. A variety of E. coli strains such as E. coli BL21, BL21 codon plus, A19, and the like, can be used for the method of the embodiment. The reason for the improvement in the protein synthetic activity of the inventive method using a linear template DNA is not exactly clear, but it is speculated that, in the E. coli extract cultured at a low temperature, the abundance of DNA degradation enzymes is decreased, or any factors inhibit mRNA degradation by these enzymes.

The cell-free protein synthesis system of the embodiment can be carried out by a batch method, flow method, and any other known techniques (refer to Spirin, A. et al., Meth. In Enzymol. volume 217, pp. 123-142, 1993). In particular, a protein synthesis system by dialysis method is preferable, which method comprises an internal and external solutions separately through a dialysis membrane (ultrafiltration membrane), and is capable of shaking and/or stirring. As a dialysis device, such as DispoDialyzer® (Spectrum), Slidealyzer® (Pierce), or Spectra/Por® dialysis tube (Spectrum), can be used. Details of the cell-free protein synthesis system using the improved dialysis method by the present applicant are disclosed in JP-A-2000-175695, and the content thereof is incorporated herein by reference.

The linear template DNA used in the embodiment is a double stranded DNA that comprises an appropriate expression control region and a gene sequence encoding a desirable protein to be expressed. To improve the expression efficiency of the protein, it is necessary to enhance the transcription by using a strong promoter and terminator, as well as the translation efficiency by increasing the affinity between mRNA and ribosomes. For example, T7 RNA polymerase derived from T7 phage is known to have an extremely higher transcriptional activity, and used for the production of recombinant protein in higher level. In addition, an introduction of a ribosome binding site (RBS) referred to as SD sequence, is important for increasing the translational efficiency. It is also possible to design a template DNA so as to synthesize a fusion protein integrating an affinity tag sequence that is useful for rapid purification or detection of synthesized protein. An improved method to effectively produce such a linear template DNA, is disclosed by the applicant in international publication pamphlet No. WO 03004703, and the content is incorporated herein by reference.

EXAMPLE

The present invention is now explained in more details by reference to the following examples, which do not intend to limit the present invention thereto.

Example 1

Culture of E. coli at Various Temperatures

Figure 2:
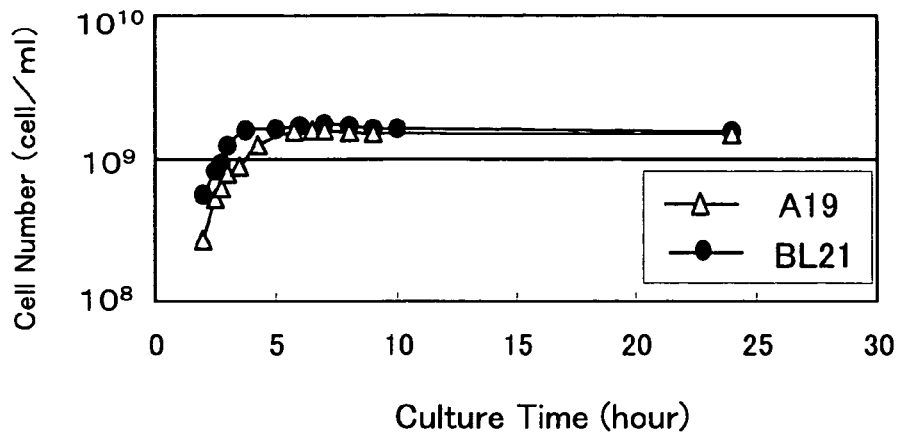
FIG. 2 shows the same results of the growth curves represented in FIG. 1, in which the longitudinal axes are represented by logarithmic plot of calculated cell numbers.
Figure 2:
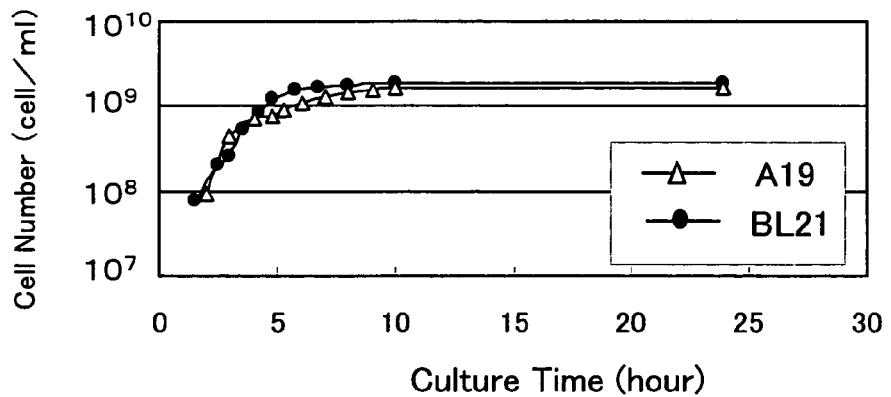
Figure 2:
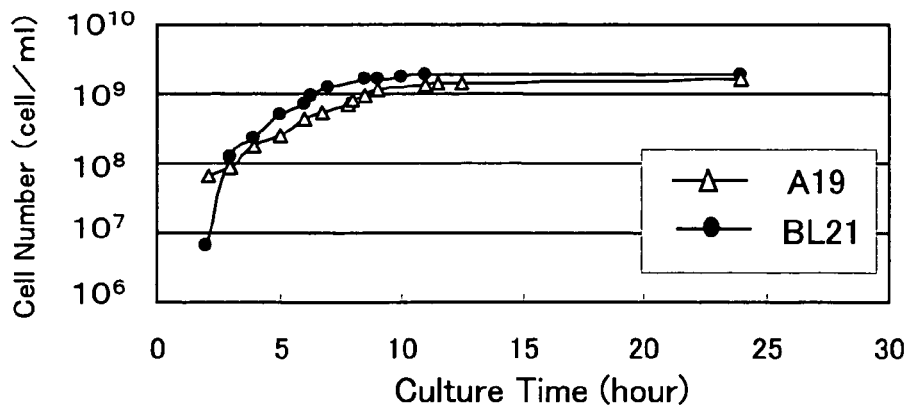

E. coli BL21 strain (F$^-$, ompT, hsdS$_B$) and A19 strain (rna, met) were cultured for overnight in a typical liquid medium to prepare seed cultures. Each of the seed cultures was inoculated into Jar fermenter containing seven liters of 2×YT medium (16 g/l Bacto Tryptone, 10 g/l Yeast Extract, and 5 g/l NaCl), and cultured at each temperature of 26° C., 30° C. and 37° C. with sufficient aeration by stirring at 400 rpm. An aliquot was removed for sampling from the culture medium sequentially until 24 hours, and the turbidities (Absorbance at 600 nm) of the samples were measured to estimate the cell numbers. The results are shown in FIG. 1. As shown in FIG. 1, the time from lag phase to logarithmic growth phase became longer when the culture temperature was getting lower, but the growth was reached to the stationary phase of almost constant turbidities after 10 to 24 hours from starting the culture. FIG. 2 is a plot of cell numbers of logarithmic scale calculated from the turbidities of growth curve shown in FIG. 1 against culture time. As shown in FIG. 2, the linear lines toward upper right show the logarithmic growth of cell numbers. The lower the temperature became, the longer the duration of the logarithmic growth phase took significantly.

Example 2

Preparation of E. coli Cell Extract and Comparison of Protein Synthesis Activity by CAT Assay The E. coli S30 extracts were prepared according to the method of Zubay et al. (vide supra) from the strains cultured in Example 1 using cells in late logarithmic growth phase (OD$_{600}$=3, about 10$^9$ cells/ml) and in stationary phase (after 24 hours), respectively. The protein synthetic reaction was carried out by adding 120 ng (4 ng/μl in total 30 μl) of pK7-CAT (CAT expression vector; see Kim et al., Eur. J. Biochem. 239, 881-886, 1996) to a solution of the composition shown in the following Table 1, to which 7.2 μl of the respective E. coli S30 extracts was further added to make 30 μl as a whole. The reaction mixture was batchwise incubated at 37° C. for 1 hour. The synthesized CAT proteins were quantified according to the method of Shaw et al. (see Methods Enzymol., 735-755, 1975). That is, the acetylation reaction of chloramphenicol by CAT was carried out using acetyl coemzyme A and chloramphenicol as substrates, and the product amount of reduced coenzyme A was determined by colorimetric assay using 5,5'-Dithiobis (2-nitrobenzoate (DTNB)). The CAT activity was calculated based on the increase of absorbance at 412 nm at 37° C. per unit time to determine the amount of CAT protein.

TABLE 1

Composition of the cell-free protein synthetic reaction mixture

| Composition | Concentration |
| --- | --- |
| HEPES-KOH pH 7.5 | 58.0 mM |
| Dithiothreitol | 2.3 mM |
| ATP | 1.2 mM |
| CTP, GTP, UTP | 0.9 mM each |
| Creatine phosphate | 81.0 mM |
| Creatine kinase | 250.0 µg/ml |
| Polyethylene glycol 8000 | 4.00% |
| 3',5'-cAMP | 0.64 mM |
| L(−)-5-Formyl-5,6,7,8-tetrahydrofolic acid | 35.0 µg/ml |
| E. coli total tRNA | 170.0 µg/ml |
| Potassium glutamate | 200.0 mM |
| Ammonium acetate | 27.7 mM |
| Magnesium acetate | 10.7 mM |
| Amino acids (20 types) | 1.0 mM each |
| T7RNA polymerase | 16.0 units/µl |

Absorbance at 260 nm of the S30 extract was measured to calculate crude ribosome content in 1 ml of the S30 extract. The amount of synthesized CAT protein per ml protein synthetic solution and that per unit ribosome amount, which was calculated according to the following equation, were shown in the following Tables 2 to 4:

Amount of synthesized CAT protein per unit ribosome=[Amount of synthesized CAT protein (µg/ml reaction solution)×0.03]/[Crude ribosome content ($A_{260}$/ml extract)×0.0072]

TABLE 2

CAT synthesis using E. coli extracts of cells cultured at 37° C.

| E. coli strain | Growth phase | Crude ribosome content (A260/ml extract) | Synthesized CAT protein (µg/ml reaction solution) | Synthesized CAT protein per unit ribosome (µg/unit ribosome) |
| --- | --- | --- | --- | --- |
| BL21 | Log phase | 224 | 650 | 12.1 |
|  | Stationary phase | 89 | 50 | 2.3 |
| A19 | Log phase | 231 | 497 | 8.6 |
|  | Stationary phase | 65 | 46 | 2.9 |

TABLE 3

CAT synthesis using E. coli extracts of cells cultured at 30° C.

| E. coli strain | Growth phase | Crude ribosome content (A260/ml extract) | Synthesized CAT protein (µg/ml reaction solution) | Synthesized CAT protein per unit ribosome (µg/unit ribosome) |
| --- | --- | --- | --- | --- |
| BL21 | Log phase | 209 | 675 | 13.4 |
|  | Stationary phase | 131 | 516 | 16.4 |
| A19 | Log phase | 202 | 405 | 8.4 |
|  | Stationary phase | 149 | 213 | 6.0 |

TABLE 4

CAT synthesis using E. coli extracts of cells cultured at 26° C.

| E. coli strain | Growth phase | Crude ribosome content (A260/ml extract) | Synthesized CAT protein (µg/ml reaction solution) | Synthesized CAT protein per unit ribosome (µg/unit ribosome) |
| --- | --- | --- | --- | --- |
| BL21 | Log phase | 209 | 566 | 11.3 |
|  | Stationary phase | 133 | 568 | 17.8 |
| A19 | Log phase | 203 | 364 | 7.5 |
|  | Stationary phase | 158 | 340 | 9.0 |

Figure 3:
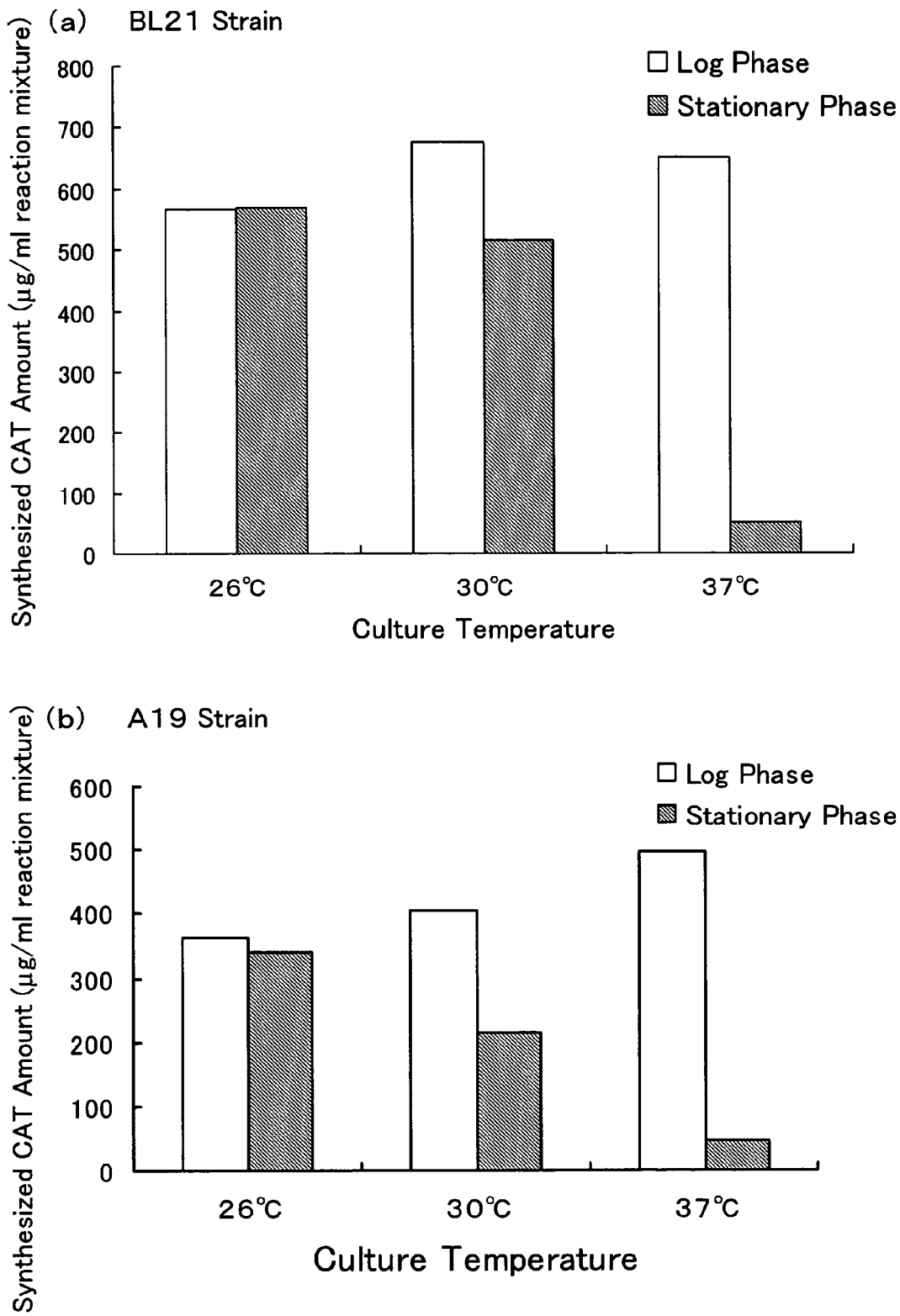
FIG. 3 are graphs that show the amounts of CAT produced in S30 extracts prepared from (a) *E. coli* BL21 strain or (b) *E. coli* A19 strain cultured at 37° C., 30° C. or 26° C.

As shown in Tables 2 to 4, crude ribosome content per 1 ml extract of stationary phase is smaller than that of log phase, however, the reduction rate of crude ribosome content in the extracts of the cells cultured at lower temperature than 37° C. (e.g. at 30° C. or 26° C.) is much smaller. The amounts of synthesized CAT protein in the extracts of the cells of both log phase and stationary phase at the each culture temperature are shown in FIG. 3. From these results, the amount of synthesized CAT protein per 1 ml of the reaction mixture was highest in the extracts prepared from cells of log phase cultured at 30 to 37° C., whereas the CAT synthetic activity of the extract prepared from the cells of stationary phase cultured at 37° C. was significantly decreased. On the other hand, the CAT synthetic activity of the extract prepared from the cells of stationary phase cultured at 30 to 26° C. was not decreased so much compared to that of log phase, in particular, the extract prepared from the cells cultured at 26° C. showed almost equal synthetic activity to that of log phase. Therefore, the amount of the synthesized CAT protein per unit ribosome was highest in the extract prepared from the cells of stationary phase cultured at 26° C., as is clearly shown by the comparison of Tables 2 to 4. These results indicate that ribosomes in cells of stationary phase cultivated at lower temperature than 37° C. are more stable than those cultivated at 37° C. It is also speculated that the protein synthetic activity of the ribosome itself cultured at lower temperature is improved.

The recoveries from the cultures at 37° C. and 26° C. using BL21 strain in Example 1 are shown as wet cell amount (g) and volume of the S30 extract (ml) in the following Table 5.

TABLE 5

| Culture temperature | Growth phase | Wet cell amount (g/7 L broth) | Volume of S30 extract (ml/7 L broth) |
|---|---|---|---|
| 37° C. | Log phase | 45.5 | 38 |
| | Stationary phase | 80.5 | 56 |
| 26° C. | Log phase | 45.5 | 38 |
| | Stationary phase | 94.5 | 66 |

From these results, the recoveries of both the wet cell amount and volume of the S30 extract at stationary phase were found to be higher than those at log phase. According to the results shown in Tables 1 to 5, the total protein amount synthesized with the extract prepared from the cells at stationary phase cultured at 26° C. was found to be highest.

Example 3

Characterization of Ribosomes

Figure 4:
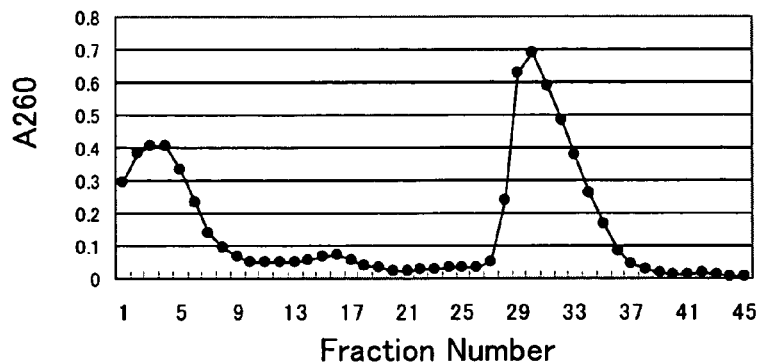
FIG. 4 shows the results of fractionation of S30 extracts by sucrose density gradient ultracentrifugation, wherein the extracts are prepared from each of logarithmic growth phase and stationary phase of *E. coli* BL21 strain cultured at 26° C. or 37° C.
Figure 4:
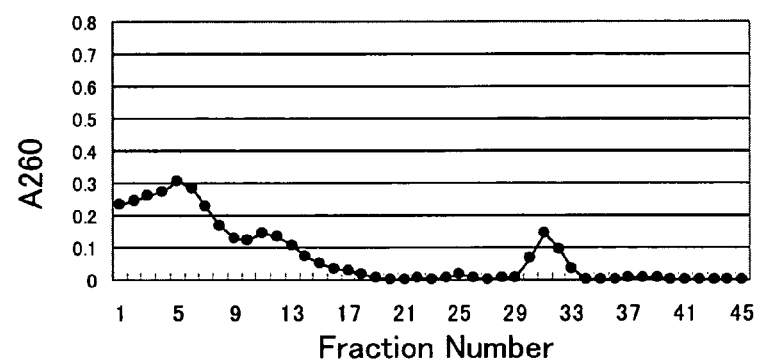
Figure 4:
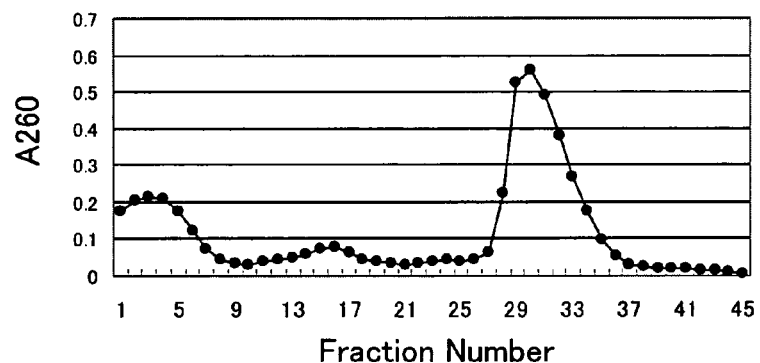
Figure 4:
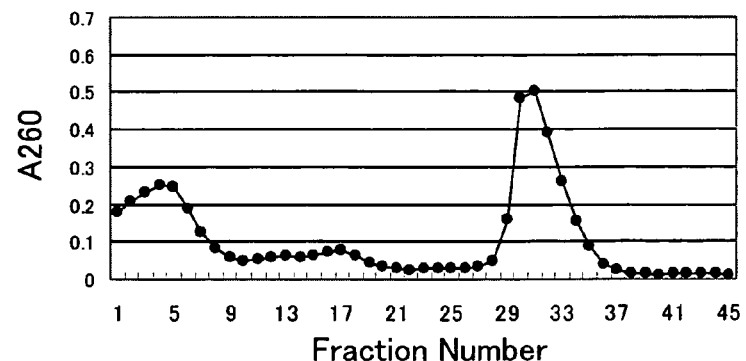

The S30 extracts were prepared according to the method of Example 2 from *E. coli* BL21 strain cultivated at each of 37° C. and 26° C. in Example 1. These extracts were loaded on the buffer (20 mM HEPES, 5 mM $MgCl_2$, 100 mM $NH_4Cl$, and 4.5 mM 2-mercaptoethanol) containing from 6 to 38% sucrose, then separated by ultracentrifugation at 17,000 rpm for 17 hours with Beckman SW 28 rotor, and fractionated into fractions of each 0.8 ml. FIG. 4 shows the result, in which the presence of ribosomal fraction is shown as absorbance at 260 nm at longitudinal axis.

In FIG. 4, the peaks around fraction Nos. 30 to 32 indicate *E. col* 70S ribosome. As shown in FIG. 4, 70S ribosome content is significantly reduced by degradation in the cells of stationary phase cultured at 37° C., whereas the degradation is rather less in the extract of cells cultured at 26° C., which indicates that 70S ribosome survives in cells of stationary phase.

Example 4

Cell-Free Protein Synthesis in Dialysis System Using a Linear Template DNA

Next, by using a linear double stranded DNA encoding CAT protein as a template, cell-free protein synthetic reactions were carried out to synthesize CAT protein in dialysis system. The linear double stranded DNA was obtained by usual polymerase chain reaction (PCR) with a CAT expression vector pK7-CAT used in Example 2, and 5' primer M13-45 Fw: 5'-CCAGGGTTTTCCCAGTCACGAC-3'(SEQ ID No: 1) and 3' primer M13 Rev: 5'-AATTTCACACAGGAAA-CAGCTATGAC-3'(SEQ ID No: 2). The composition of reaction mixture is shown in Table 6. After initial denaturation at 94° C. for 2 minutes, the PCR was carried out with a cycle at 94° C. for 30 seconds, at 53° C. for 30 seconds, and at 72° C. for 2 minutes for ten times; a cycle at 94° C. for 30 seconds, at 53° C. for 30 seconds, and at 72° C. for 2 minute plus 5 seconds in every cycle for 20 times; and finally one cycle of elongation reaction at 72° C. for 5 minutes.

TABLE 6

| | |
|---|---|
| Template DNA (pK7-CAT) | 50 pg |
| 10x HiFi PCR buffer | 5 μl |
| 5'-primer (10 μM) | 5 μl |
| 3'-primer(10 μM) | 5 μl |
| 2.5 mM dNTPs | 5 μl |
| Expand HiFi DNA polymerase | 0.35 μl |
| Fill up to 50 μl with water | |
| Total volume | 50 μl |

Thus prepared linear template DNA or the circular plasmid pK7-CAT, and *E. coli* extracts prepared by the same method of Example 1, were used for performing cell-free protein synthesis by dialysis system.

*E. coli* used herein was a strain BL21 codon plus, and cultured until stationary phase (24 hours from start of culture) according to the same method of Example 1. The S30 extracts were prepared according to the method of Zubay et al. (Zubay et al., Annu. Rev. Geneti., 7, 267-287, 1973) from these cells. Protein synthetic reaction by dialysis system was performed at 30° C. for 8 hours using a reaction solution whose composition is shown in Table 7, and dialyzed against the external solution whose composition is shown in Table 8. The reaction scale is 30 μl of the reaction solution, and 300 μl of external solution, in which each 0.5, 1, 2, or 4 μg/ml of linear DNA or circular plasmid was added to the reaction solution.

TABLE 7

Composition of protein synthetic reaction mixture

| Composition | Concentration |
|---|---|
| HEPES-KOH, pH 7.5 | 58.0 mM |
| Dithiothreitol (DTT) | 1.8 mM |
| ATP | 1.2 mM |
| CTP, GTP, UTP | 0.8 mM each |
| Creatine phosphate | 80.0 mM |
| Creatine kinase | 0.25 mg/ml |
| Polyethylene glycol 8000 | 4.0% |
| 3',5'-cAMP | 0.64 mM |
| L(−)-5-Formyl-5,6,7,8-tetrahydrofolic acid | 68 μM |
| *E. coli* total tRNA | 175 μg/ml |
| Potassium glutamate | 210.0 mM |
| Ammonium acetate | 27.5 mM |
| Magnesium acetate | 10.7 mM |
| Amino acids (20 types) | 1.5 mM each |
| Sodium azide | 0.05% |
| T7 RNA polymerase | 66.6 μg/ml |
| *E. coli* S30 extract | 30 vol. % of the reaction mixture |
| Template DNA | 0.5-4 μg/ml |

TABLE 8

Composition of external solution

| Composition | Concentration |
|---|---|
| HEPES-KOH, pH 7.5 | 58.0 mM |
| Dithiothreitol (DTT) | 1.8 mM |
| ATP | 1.2 mM |
| CTP, GTP, UTP | 0.8 mM each |
| Creatine phosphate | 80.0 mM |
| Creatine kinase | 0.25 mg/ml |
| Polyethylene glycol 8000 | 4.0% |
| 3',5'-cAMP | 0.64 mM |
| L(−)-5-Formyl-5,6,7,8-tetrahydrofolic acid | 68 μM |

TABLE 8-continued

Composition of external solution

| Composition | Concentration |
| --- | --- |
| Potassium glutamate | 210.0 mM |
| Ammonium acetate | 27.5 mM |
| Magnesium acetate | 14.9 mM |
| Amino acids (20 types) | 1.5 mM each |
| Sodium azide | 0.05% |
| Tris-acetate (pH 8.2) | 3 mM |
| Potassium acetate | 18 mM |

Figure 5:
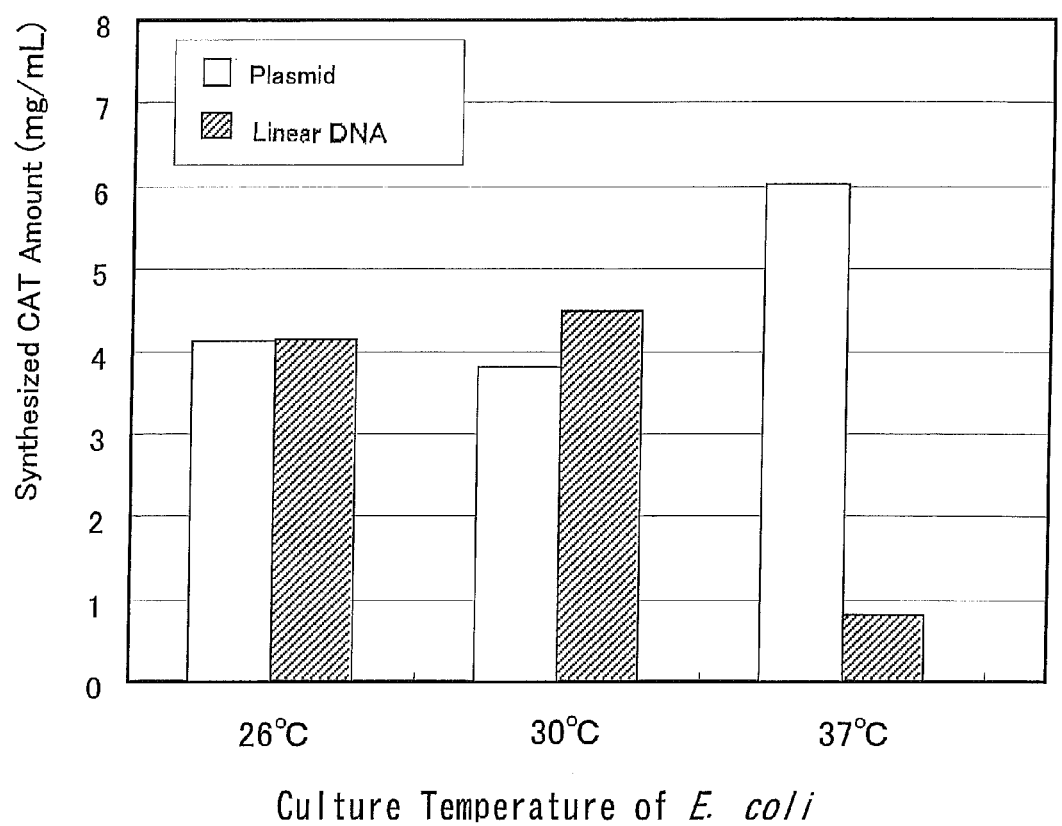
FIG. 5 shows the amounts of CAT synthesized in the cell-free protein synthesis system (dialysis system) using S30 extracts prepared from *E. coli* BL21 codon plus cultured at 37° C., 30° C. or 26° C., and a template either plasmid or linear DNA.

FIG. 5 shows the amount of CAT synthesized in the dialysis system using E. coli cell extracts prepared from the cells cultured until stationary phase at each of 26° C., 30° C., and 37° C., and 1 μg/ml linear DNA (linear) or circular plasmid (Plasmid) as a template. The extracts prepared from E. coli cultured at 37° C. showed higher CAT synthesis when the plasmid DNA was used as a template, whereas the synthetic amount was decreased significantly when the linear DNA was used as a template. On the contrary, the extracts prepared from E. coli cultured at each of 26° C. and 30° C. showed almost equal amount of CAT synthesized in both cases using the plasmid DNA and linear DNA as a template. Comparing the results using the linear DNA as a template, it is clear that the extract prepared from E. coli of stationary phase cultured at lower temperature shows a superior CAT synthetic activity to that cultured at higher temperature.

Figure 6:
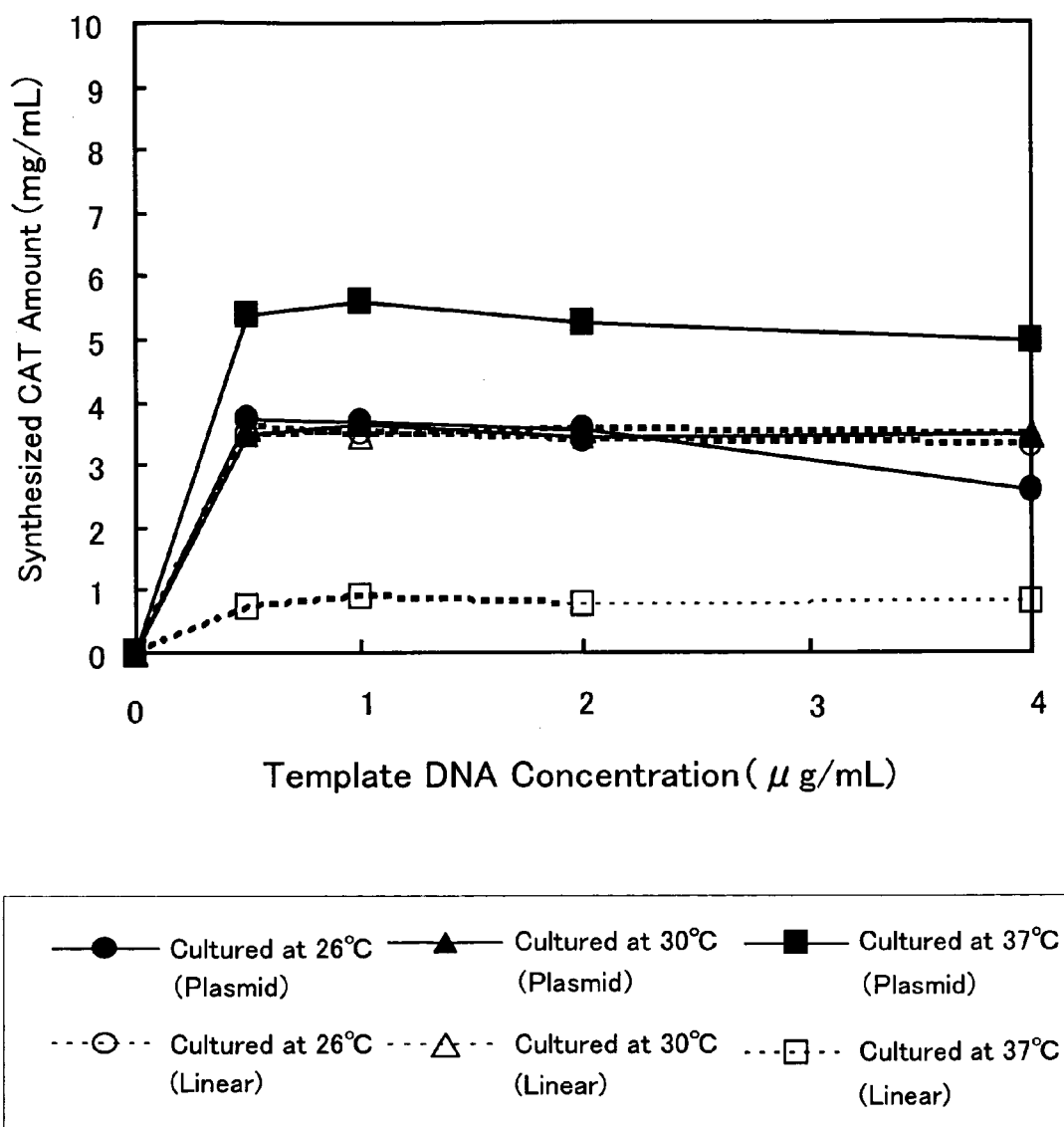
FIG. 6 shows the amounts of CAT synthesized in the cell-free protein synthesis system (dialysis system) using S30 extracts prepared from *E. coli* BL21 codon plus cultured at 37° C., 30° C. or 26° C., and a template either various concentrations of plasmid or linear DNA.

FIG. 6 shows the results of similar experiments adding variable amounts of template DNAs. As shown in FIG. 6, the amount of added template DNA is sufficient in a concentration of about 1 μg/ml.

INDUSTRIAL APPLICABILITY

The extract for use in a cell-free protein synthesis produced by the method of the present invention, keeps the elevated protein synthetic activity, as well as can be obtained in a larger amount than prior method. In addition, due to the easy control of culture time, the working efficiency is improved. In particular, the effect is significant when a linear template DNA such as a PCR product is used as a template. Therefore, the present invention is critically useful for expression of a variety of proteins and comprehensive analysis of their structures and functions.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

What is claimed is:

1. A process for performing a cell-free protein synthesis comprising the steps of:
 culturing a bacterial cell under a suppressed growth condition, wherein said suppressed growth condition comprises a temperature of from 20° C. to 32° C.,
 harvesting the bacterial cell at a stationary phase in said culture,
 disrupting said harvested cell to obtain an extract, and
 performing cell free protein synthesis using said extract.

2. The process of claim 1, wherein said cell is *Escherichia coli*.

3. A process for performing a cell-free protein synthesis comprising the steps of:
 culturing *Escherichia coli* cells under a suppressed growth condition, wherein said suppressed growth conditions comprises a temperature of from 20° C. to 32° C.,
 harvesting the *Escherichia coli* cells at a stationary phase of said culture,
 preparing S30 extract from said harvested *Escherichia coli* cells, and
 performing cell free protein synthesis using said S30 extract.

4. The process of claims 1, 2 or 3, wherein said cell-free protein synthesis is carried out using a linear template DNA.

5. The process of claim 4, wherein said cell-free protein synthesis is a dialysis system.

* * * * *